(12) United States Patent
Kheradvar (10) Patent No.: US 8,876,897 B2
(45) Date of Patent: Nov. 4, 2014

(54) IMPLANTABLE PROSTHETIC VALVES AND METHODS RELATING TO SAME

(75) Inventor: Arash Kheradvar, Blythewood, SC (US)

(73) Assignee: Arash Kheradvar, Irvine, CA (US)

( * ) Notice: Subject to any disclaimer, the term of this patent is extended or adjusted under 35 U.S.C. 154(b) by 108 days.

(21) Appl. No.: 12/341,170

(22) Filed: Dec. 22, 2008

(65) Prior Publication Data

US 2009/0164003 A1    Jun. 25, 2009

Related U.S. Application Data (60) Provisional application No. 61/008,599, filed on Dec. 20, 2007.

(51) Int. Cl.
    *A61F 2/24* (2006.01)

(52) U.S. Cl.
    CPC ............ *A61F 2/2412* (2013.01); *A61F 2/2442* (2013.01); *A61F 2/2445* (2013.01); *A61F 2230/0008* (2013.01); *A61F 2210/0014* (2013.01); *A61F 2230/0095* (2013.01); *A61F 2230/0078* (2013.01)
    USPC ....... 623/2.36; 623/2.16; 623/2.14; 623/2.12; 623/2.13; 623/2.17; 623/2.18

(58) Field of Classification Search
    USPC .............................. 623/2.12–2.19
    See application file for complete search history.

(56) References Cited

U.S. PATENT DOCUMENTS

| | | |
|---|---|---|
| 4,451,936 A | 6/1984 | Carpentier et al. |
| 4,759,758 A | 7/1988 | Gabbay |
| 4,790,843 A | 12/1988 | Carpentier et al. |
| 4,994,077 A | 2/1991 | Dobben |
| 5,163,953 A | 11/1992 | Vince |
| 5,332,402 A | 7/1994 | Teitelbaum |
| 5,370,685 A | 12/1994 | Stevens |
| 5,397,351 A | 3/1995 | Pavcnik et al. |
| 5,411,552 A | 5/1995 | Andersen et al. |
| 5,445,626 A | 8/1995 | Gigante |
| 5,500,014 A | 3/1996 | Quijano et al. |
| 5,824,064 A | 10/1998 | Taheri |
| 5,840,081 A | 11/1998 | Andersen et al. |
| 5,855,597 A | 1/1999 | Jayaraman |
| 5,855,601 A | 1/1999 | Bessler et al. |
| 5,925,063 A | 7/1999 | Khosravi |
| 5,954,766 A | 9/1999 | Zadno-Azizi et al. |
| 5,957,949 A | 9/1999 | Leonhardt et al. |
| 6,077,298 A | 6/2000 | Tu et al. |
| 6,106,550 A | 8/2000 | Magovern et al. |
| 6,168,614 B1 | 1/2001 | Andersen et al. |

(Continued)

*Primary Examiner* — David Isabella
*Assistant Examiner* — Jacqueline Woznicki
(74) *Attorney, Agent, or Firm* — Tope-McKay & Associates (57) ABSTRACT

In accordance with one embodiment of the present disclosure, a prosthetic valve is provided. The prosthetic valve includes an annulus, a pair of leaflets, and a pair of support elements. The annulus has a generally saddle-shape formed by a movable pair of first portions separated from each other by a movable pair of second portions. The pair of leaflets extend from the annulus and are separated from each other by the pair of support elements. The first portions of the annulus and the second portions of the annulus are configured to move back and forth from being generally concave to being generally convex such that any movement of the first portions of the annulus occurs at generally the same time as any movement of the second portions of the annulus.

8 Claims, 3 Drawing Sheets

(56) References Cited

U.S. PATENT DOCUMENTS

| | | |
|---|---|---|
| 6,206,911 B1 | 3/2001 | Milo |
| 6,283,127 B1 | 9/2001 | Sterman et al. |
| 6,530,952 B2 | 3/2003 | Vesely |
| 6,569,196 B1 | 5/2003 | Vesely |
| 6,582,462 B1 | 6/2003 | Andersen et al. |
| 6,652,578 B2 | 11/2003 | Bailey et al. |
| 6,830,584 B1 | 12/2004 | Seguin |
| 6,830,585 B1 | 12/2004 | Artof et al. |
| 6,890,350 B1 | 5/2005 | Walak |
| 6,896,690 B1 | 5/2005 | Lambrecht et al. |
| 6,908,481 B2 | 6/2005 | Cribier |
| 6,951,571 B1 | 10/2005 | Srivastava |
| 6,974,464 B2 | 12/2005 | Quijano et al. |
| 6,974,476 B2 | 12/2005 | McGuckin, Jr. et al. |
| 7,011,681 B2 | 3/2006 | Vesely |
| 7,041,132 B2 | 5/2006 | Quijano et al. |
| 7,331,991 B2 | 2/2008 | Kheradvar et al. |
| 2004/0117009 A1* | 6/2004 | Cali et al. .............. 623/2.12 |
| 2005/0004668 A1* | 1/2005 | Aklog et al. ........... 623/2.36 |
| 2005/0131533 A1* | 6/2005 | Alfieri et al. .......... 623/2.36 |
| 2006/0216173 A1 | 9/2006 | Kheradvar et al. |
| 2008/0161909 A1 | 7/2008 | Kheradvar et al. |
| 2008/0275550 A1 | 11/2008 | Kheradvar et al. |

* cited by examiner

IMPLANTABLE PROSTHETIC VALVES AND METHODS RELATING TO SAME

CROSS-REFERENCE TO RELATED APPLICATION

The present application is based on and claims priority to U.S. Provisional Application 61/008,599 having a filing date of Dec. 20, 2007, which is incorporated by reference herein.

BACKGROUND

Human heart valves under the conditions of normal physiological functions are organs that open under the changes in pressure gradient inside the cardiac chambers. Four valves in the heart serve to direct the flow of blood through all chambers in a forward direction. In addition to the four heart valves (tricuspid valve, mitral valve, aortic valve, and pulmonary valve), a patient has other flow-regulatory valves, such as venous valves, sphincter valves, and the like.

When disease conditions affect the structure or the materials of the native valve, the valve itself will decay, degenerate or disrupt and requires repair or replacement to restore proper function necessary for the continuation of life.

U.S. Pat. No. 4,451,936 to Carpentier et al., entire contents of which are incorporated herein by reference, discloses an aortic prosthetic valve for supra-annular implantation comprising a valve body of generally annular configuration and a valve element movably mounted on the valve body for opening and closing the valve, and a scalloped suture ring circumscribing the valve body adjacent the base surface and configured to approximately fit the contour of the Sinuses of Valsalva at the base of the aorta.

U.S. Pat. No. 4,790,843 to Carpentier et al., entire contents of which are incorporated herein by reference, discloses a prosthetic heart valve assembly that includes an artificial annulus, a prosthetic valve and a retaining ring for releasably retaining the prosthetic valve on the artificial annulus. By removing the retaining ring, the valve can be replaced with another valve.

U.S. Pat. No. 4,759,758 to Gabbay, entire contents of which are incorporated herein by reference, discloses an improved prosthetic heart valve comprising a support body or stent covered by a layer of biological tissue having only the smooth surfaces thereof presented outwardly. The valve cusp is made of pericardial tissue that has been doubled over such that the rough side thereof is folded inwardly.

U.S. Pat. No. 4,994,077 to Dobben, entire contents of which are incorporated herein by reference, discloses a valve system consisting of a cylindrical or crown shaped stent that is made by bending wire into a zigzag shape to anchor the device and attach the flow regulator flap of a valve. The device presents significant hemodynamic, delivery, fatigue and stability disadvantages.

U.S. Pat. No. 5,163,953 to Vince, entire contents of which are incorporated herein by reference, discloses a valve system consisting of a flow-regulation mechanism of a flap of biologic material that is mounted inside a stent comprised of a toroidal body formed of a flexible coil of wire. The main shortcoming of this design is the profile and configuration, thus making the device clinically ineffective as a minimally invasive technique.

U.S. Pat. No. 5,332,402 to Teitelbaum, entire contents of which are incorporated herein by reference, discloses a valve system consisting of shape memory Nitinol and a flow-regulating valve. The stent-like support is comprised of a meshwork or braiding of Nitinol wire with trumpet-like distal and proximal flares. The flared ends are intended to maintain the position of the stent component across the valve thereby anchoring the device. The disadvantages of the device are the reduced valve orifice and sub-optimal hemodynamic characteristics.

U.S. Pat. No. 5,370,685 to Stevens, entire contents of which are incorporated herein by reference, discloses a percutaneous valve replacement system for the endovascular removal of a malfunctioning valve followed by replacement with a prosthetic valve. The valve replacement system may include a prosthetic valve device comprised of a stent and cusps for flow-regulation such as a fixed porcine aortic valve, a valve introducer, an intraluminal procedure device, a procedure device capsule and a tissue cutter. The valve device disclosed requires a large delivery catheter and intraluminal-securing means such as suturing to anchor the device at the desired location.

U.S. Pat. No. 5,397,351 to Pavcnik et al., entire contents of which are incorporated herein by reference, discloses a self-expanding percutaneous valve comprised of a poppet, a stent and a restraining element. The valve stent has barbed means to anchor to the internal passageway. The device includes a self-expanding stent of a zigzag configuration in conjunction with a cage mechanism comprised of a multiplicity of criss-crossed wires and a valve seat. The disadvantages of the device include large delivery profile, reduced effective valvular orifice, and possible perivalvular leakage.

U.S. Pat. No. 5,411,552 to Andersen et al., entire contents of which are incorporated herein by reference, discloses various balloon expandable percutaneous prosthetic valves. One embodiment discloses a valve prosthesis comprised of a stent made from an expandable cylindrical structure and an elastically collapsible valve mounted to the stent. The device is placed at the desired location by balloon expanding the stent and the valve. The main disadvantage to this design is the 20+ French size delivery catheters.

U.S. Pat. No. 5,445,626 to Gigante, entire contents of which are incorporated herein by reference, discloses a valve operated catheter for urinary incontinence and retention comprising a flexible duct designed to be inserted in the patient's urethra, the catheter provided with a spiral shaped end portion, having a plurality of holes for the passage of urine. The duct is provided, at its other end, with a seat in which there is housed a valve made of elastic material, the valve being usually closed because of the elastic action.

U.S. Pat. No. 5,500,014 to Quijano et al., entire contents of which are incorporated herein by reference, discloses a biological valvular prosthesis comprising a chemically fixed conduit derived from a harvested vein segment bearing at least one integrally formed venous valve, and a restriction means positioned about the conduit at either side of the venous for restricting the venous valve from expanding outwardly.

U.S. Pat. No. 5,824,064 to Taheri, entire contents of which are incorporated herein by reference, discloses an aortic valve replacement system combined with an aortic arch graft. The devices and percutaneous methods described require puncture of the chest cavity.

U.S. Pat. No. 5,840,081 to Andersen et al., entire contents of which are incorporated herein by reference, discloses a valve prosthesis for implantation in the body by use of a catheter. The valve prosthesis is formed of a stent with a pre-formed collapsible valve mounted on the stent.

U.S. Pat. No. 5,855,597 to Jayaraman, entire contents of which are incorporated herein by reference, discloses a device comprising a star-shaped stent, a replacement valve and a replacement graft for use in repairing a damaged cardiac valve. The device is comprised of a chain of interconnected star-shaped stent segments in the center of which sits a replacement valve. The flow-regulation mechanism consists of three flaps cut into a flat piece of graft material that is rolled to form a conduit in which the three flaps may be folded inwardly in an overlapping manner.

U.S. Pat. No. 5,855,601 to Bessler et al., entire contents of which are incorporated herein by reference, discloses methods and devices for the endovascular removal of a defective heart valve and the replacement with a percutaneous cardiac valve. The device is comprised of a self-expanding stent member with a flexible valve disposed within. The stent member is of a self-expanding cylindrical shape made from a closed wire in a zigzag configuration that can be a single piece, stamped, extruded or formed by welding the free ends together. The flow-regulation mechanism is comprised of an arcuate portion that contains a slit to form leaflets and a cuff portion that is sutured to the stent and encloses the stent. The preferred flow regulator is a porcine pericardium with three cusps.

U.S. Pat. No. 5,925,063 to Khosravi, entire contents of which are incorporated herein by reference, discloses a percutaneous prosthetic valve comprised of a coiled sheet stent to which a plurality of flaps are mounted on the interior surface to form a flow-regulation mechanism that may be comprised of a biocompatible material. The disadvantages of this design include problematic interactions between the stent and flaps in the delivery state, and the lack of a detailed mechanism to ensure that the flaps will create a competent one-directional valve.

U.S. Pat. No. 5,954,766 to Zadano-Azizi et al., entire contents of which are incorporated herein by reference, discloses a device in which flow-regulation is provided by a flap disposed within a frame structure capable of taking an insertion state and an expanded state. The preferred embodiment of the flow-regulation mechanism is defined by a longitudinal valve body made of a sufficiently resilient material with a slit that extends longitudinally through the valve body.

U.S. Pat. No. 5,957,949 to Leonhardt et al., entire contents of which are incorporated herein by reference, discloses a prosthetic valve comprised of a tubular graft having radially compressible annular spring portions and a flow regulator, which is preferably a biological valve disposed within. In addition to oversizing the spring stent by 30%, anchoring means is provided by a light-activated biocompatible tissue adhesive that is located on the outside of the tubular graft and seals to the living tissue. Disadvantages of this device include those profile concerns, a large diameter complex delivery system, and feasibility of the light actuated anchoring means.

U.S. Pat. No. 6,106,550 to Magovern et al., entire contents of which are incorporated herein by reference, discloses an implantable apparatus for receiving a heart valve, comprising an annular ring having an inner wall and an outer wall, a plurality of channels displaced circumferentially about the ring, each channel extending from the inner wall to the outer wall, and a plurality of tissue attachment pins each pin being movable in a respective one of the channels between a first position during implantation, and a second position wherein the first end of each pin extends beyond the outer wall for tissue attachment.

U.S. Pat. No. 6,168,614 to Andersen et al., entire contents of which are incorporated herein by reference, discloses a method of endovascularly delivering a valve through a blood vessel, comprising the steps of providing a tissue valve and an expandable support structure, connecting the tissue valve to the support structure, and securing the tissue valve and the support structure to a desired valve location with the support structure in the expanded shape.

U.S. Pat. No. 6,206,911 to Milo, entire contents of which are incorporated herein by reference, discloses an expandable stent that is created so as to undergo essentially no axial foreshortening when expanded from an unexpanded or compressed configuration to an operative configuration. Attachment to the surrounding tissue may be via pairs of needle-like projections or prongs that may be bent to have a radial orientation during the deployment phase.

U.S. Pat. No. 6,283,127 to Sterman et al., entire contents of which are incorporated herein by reference, discloses a device system and methods facilitating intervention within the heart or a great vessel without the need for a median sternotomy or other form of gross thoracotomy, substantially reducing trauma, risk of complication, recovery time, and pain for the patient. Using the device systems and methods of the invention, surgical procedures may be performed through percutaneous penetrations within intercostal spaces of the patient's rib cage, without cutting, removing, or significantly displacing any of the patient's ribs or sternum.

U.S. Pat. No. 6,530,952 to Vesely, entire contents of which are incorporated herein by reference, discloses a cardiovascular valve system including a permanent base unit that is affixed to the patient using conventional sutures or staples, and a collapsible valve having a collapsible frame that mates with the permanent base unit, and supports valve leaflets. An installed collapsible frame may be re-collapsed and disengaged from the permanent housing whereas a new collapsible valve is then installed, to resume the function of the prosthesis.

U.S. Pat. No. 6,569,196 to Vesely, entire contents of which are incorporated herein by reference, discloses a system for minimally invasive insertion of a bioprosthetic heart valve. The system includes a collapsible tissue-based valve system, a catheter-based valve delivery system, a surgical platform and a device tracking and visualization system, wherein the collapsible valve system includes a permanent outer frame that is affixed to the patient using conventional sutures or staples and a collapsible valve having a collapsible inner frame that mates with the outer frame.

U.S. Pat. No. 6,582,462 to Andersen et al., entire contents of which are incorporated herein by reference, discloses a valve prosthesis for implantation in a body channel by way of catheterization, the prosthesis comprising a radially collapsible and expandable cylindrical stent and a collapsible and expandable valve having commissural points wherein the valve is mounted to the stent at the commissural points.

U.S. Pat. No. 6,652,578 to Bailey et al., entire contents of which are incorporated herein by reference, discloses a catheter system with minimally invasive techniques for percutaneous and transluminal valvuloplasty and prosthetic valve implantation.

U.S. Pat. No. 6,830,584 to Seguin, entire contents of which are incorporated herein by reference, discloses a device for replacing, via a percutaneous route, a heart valve located in a bodily vessel, comprising an elongated support element, two series of elongated blades arranged around the circumference of the elongated elements, where the blades have opposite cutting edges and can be extended corolla-shaped such that their cutting edges are set in the extension of one another thereby forming circular cutting edges to cut the native valve so as to separate it from the corporeal duct.

U.S. Pat. No. 6,830,585 to Artof et al., entire contents of which are incorporated herein by reference, discloses a percutaneously deliverable heart valve with a plurality of valvular leaflets, the plurality of leaflets being sewn together at least a portion of their side edges to form an annulus at about the in-flow edge and a plurality of commissure tissues.

U.S. Pat. No. 6,896,690 to Lambrecht et al., entire contents of which are incorporated herein by reference, discloses a device for performing intravascular procedures wherein at least a portion of the device is configured for placement in a flowpath of a blood vessel. The device comprises a valve means configured to allow greater antegrade flow than retrograde flow through the vessel and a filter operative to restrict the passage of emboli while allowing blood flow through the vessel.

U.S. Pat. No. 6,908,481 to Cribier, entire contents of which are incorporated herein by reference, discloses a valve prosthesis comprising a collapsible, elastic valve member, an elastic stent member in which the valve member is mounted, and a support coupled to the valve member and positioned between the valve member and the stent member, wherein the stent member forms a continuous surface and comprises strut members that provide a structure sufficiently rigid to prevent eversion.

U.S. Pat. No. 6,951,571 to Srivastava, entire contents of which are incorporated herein by reference, discloses a valve-implanting device comprising a collapsible frame, inner and outer guide wires removably connected to the collapsible frame, and a plurality of valve flaps attached to the collapsible frame.

U.S. Pat. No. 6,974,464 to Quijano, et al., entire contents of which are incorporated herein by reference, discloses a supportless atrioventricular valve intended for attaching to a circumferential valve ring and papillary muscles of a patient comprising a singular flexible membrane of tissue or synthetic biomaterial, wherein a minimally invasive delivery system is provided through a percutaneous intercostal penetration and a penetration at the cardiac wall into a left atrium of the heart.

U.S. Pat. No. 6,974,476 to McGuckin, Jr. et al., entire contents of which are incorporated herein by reference, discloses a valve system comprising a first substantially annular portion adapted to be positioned on a proximal side of the annulus of a patient and a second substantially annular portion adapted to be positioned on a distal side of the annulus of a patient, wherein at least one of the first and second substantially annular portions is movable towards the other portion to a clamped position to clamp around the annulus. The second portion has a flow restricting apparatus.

U.S. Pat. No. 7,011,681 to Vesely, entire contents of which are incorporated herein by reference, discloses a cardiovascular valve system including a permanent base unit that is affixed to the patient using conventional sutures or staples, and a collapsible valve having a collapsible frame that mates with the permanent base unit, and supports valve leaflets. An installed collapsible frame may be re-collapsed and disengaged from the permanent housing. A new collapsible valve is then installed, to resume the function of the prosthesis.

U.S. Pat. No. 7,041,132 to Quijano, et al., entire contents of which are incorporated herein by reference, discloses a percutaneous delivered heart valve and delivery means thereof, wherein the percutaneous delivered heart valve is a twistedly foldable heart valve prosthesis comprising a generally cylindrical support element with a diameter, wherein the support element is twistedly foldable to a smaller diameter, a flexible heart valve with a plurality of valvular leaflets releasably attached to said support element, and a receptacle having a plurality of connecting members secured to the cylindrical support element, wherein the receptacle is releasably matched to an expanding element capable of untwisting the receptacle adapted for un-twisting and unfolding said heart valve.

U.S. Pat. No. 7,331,991 to Kheradvar, et al., entire contents of which are incorporated herein by reference, discloses an implantable prosthetic valve that is transformable from a first helical pre-implantation configuration to a second valvular functional configuration, and methods of delivery.

Such various prior art valve designs attempt to replicate the function of native valves. However, there is an ongoing need for implantable prosthetic valves that can satisfactorily replace native valves.

Thus, a need exists for an improved prosthetic valve design. Methods relating to such a valve would also be desirable.

SUMMARY

In accordance with one embodiment of the present disclosure, a prosthetic valve is provided. The prosthetic valve includes an annulus, a pair of leaflets, and a pair of support elements. The annulus has a generally saddle-shape formed by a movable pair of first portions separated from each other by a movable pair of second portions. The pair of leaflets extend from the annulus and are separated from each other by the pair of support elements. The first portions of the annulus and the second portions of the annulus are configured to move back and forth from being generally concave to being generally convex such that any movement of the first portions of the annulus occurs at generally the same time as any movement of the second portions of the annulus. The pair of leaflets are configured to define an opening when the first portions of the annulus are each generally concave and the second portions of the annulus are each generally convex. The pair of leaflets are configured to define a seal when the first portions of the annulus are each generally convex and the second portions of the annulus are each generally concave.

In certain embodiments, the annulus and the pair of support elements can comprise a shape memory material, such as a nickel titanium alloy. The pair of leaflets can comprise synthetic material, engineered biological tissue, biological valvular leaflet tissue, pericardial tissue, cross-linked pericardial tissue, or combinations thereof. The material or tissue can comprise a compliant membrane of a single sheet or a compound manifold. In certain embodiments, the pericardial tissue can be selected from the group consisting of bovine, equine, porcine, ovine, human tissue, or combinations thereof.

In certain embodiments, one support element can be adjacent to one second portion of the annulus and the other support element can be adjacent to the other second portion of the annulus. The support elements can be curved away from one another when the pair of leaflets define a seal or can be curved towards one another when the pair of leaflets define an opening. The pair of leaflets can be configured to define a seal during systole or can be configured to define an opening during diastole.

In another embodiment of the present disclosure, a prosthetic valve is provided. A prosthetic valve includes an annulus, a pair of leaflets, and a pair of support elements. The annulus has a generally saddle-shape formed by a movable pair of first portions separated from each other by a movable pair of second portions. The pair of leaflets extend from the annulus and are separated from each other by the pair of support elements with one support element being adjacent to one second portion of the annulus and the other support element being adjacent to the other second portion of the annulus. The first portions of the annulus and the second portions of the annulus are configured to move back and forth from being generally concave to being generally convex such that any movement of the first portions of the annulus occurs at generally the same time as any movement of the second portions of the annulus. The pair of leaflets are configured to define an opening when the first portions of the annulus are each generally concave, the second portions of the annulus are each generally convex, and the support elements are curved towards one another. The pair of leaflets are configured to define a seal when the first portions of the annulus are each generally convex, the second portions of the annulus are each generally concave, and the support elements are curved away from one another.

In yet another embodiment of the present disclosure, a method of implanting a prosthetic valve in a patient is provided. The method includes delivering a prosthetic valve to an implant site in a patient and deploying the prosthetic valve at the implant site.

Other features and aspects of the present disclosure are discussed in greater detail below.

BRIEF DESCRIPTION OF THE DRAWINGS

A full and enabling disclosure, including the best mode thereof, directed to one of ordinary skill in the art, is set forth more particularly in the remainder of the specification, which makes reference to the appended figures in which:

FIG. 1 illustrates a prosthetic valve in a closed configuration from different perspective views in accordance with certain embodiment of the present disclosure including A) from top, B) trimetric, C) from a concave side, D) from a convex side;

FIG. 2 illustrates a prosthetic valve in an open configuration from different perspective views in accordance with certain embodiment of the present disclosure including A) from top, B) trimetric, C) from a convex side, D) from a concave side.

DETAILED DESCRIPTION

Reference now will be made in detail to various embodiments of the disclosure, one or more examples of which are set forth below. Each example is provided by way of explanation of the disclosure, not limitation of the disclosure. In fact, it will be apparent to those skilled in the art that various modifications and variations can be made in the present disclosure without departing from the scope or spirit of the disclosure. For instance, features illustrated or described as part of one embodiment, can be used on another embodiment to yield a still further embodiment. Thus, it is intended that the present disclosure covers such modifications and variations as come within the scope of the appended claims and their equivalents.

The present disclosure is generally directed to a prosthetic valve. For instance, in certain embodiments of the present disclosure, a bi-leaflet prosthetic valve is provided that can replace a dysfunctional heart valve or any other similar organ such as but not limited to venous valves. While the present discussion is related to bi-leaflet valves, it should be understood that other constructions are possible and contemplated by the present disclosure including, but not limited to, tri-leaflet and quad-leaflet valves.

The prosthetic valves of the present disclosure include a saddle-shaped annulus that can be attached to the proximal end of one or more leaflets to create a one-way valve system. It has been advantageously determined that the saddle-shaped annulus can transform its shape due to pressure change and that the geometrical transformation can result in the opening or closure of the prosthetic valve. Portions of the annulus are configured to move back and forth from being generally concave to being generally convex with such movement between different portions occurring almost simultaneously. In this manner, the prosthetic valve can open or close during systole or diastole, depending on the position of the valve, in embodiments in which the prosthetic valve is implemented as a heart valve.

Turning to FIGS. 1 and 2, a prosthetic valve 10 in accordance with certain embodiments of the present disclosure is illustrated. The valve 10 includes a body 12. The body 12 can include an annulus 18 having a generally saddle-shaped periphery 20. In this regard, the term "saddle-shaped" is well understood in the art but generally refers to a geometry in which the periphery 20 includes one or more ridges that connect two higher elevations.

In particular, referring again to FIGS. 1 and 2, the periphery 20 includes a pair of first periphery portions 22 and second periphery portions 24. The periphery portions 22, 24 are movable with each of the first periphery portions 22 being separated from one another by each of the second periphery portions 24, and vice versa. Importantly, the first periphery portions 22 are designed to move at generally the same time as the second periphery portions 24, and vice versa. The periphery portions 22, 24 can be integral to form periphery 20 or can be separately formed from one or more suitable materials and joined together using any suitable method as would be understood in the art.

The prosthetic valve 10 also includes a pair of leaflets 14 and a pair of support elements 16. The pair of leaflets 14 and the pair of support elements 16 extend from the superior surface of the body 12. Each of the leaflets 14 are separated from one another by each of the support elements 16, and vice versa. The support elements 16 can be of any suitable shape, such as a rod shape as illustrated. The leaflets 14 can be joined to the support elements 16 by any suitable method as would be known in the art such as by stitching, adhesives, or the like. Similarly, the leaflets 14 and support elements 16 can each be joined to body 12 by any suitable method as would be known in the art.

The leaflets 14 can be made of any suitable synthetic material, engineered biological tissue, biological valvular leaflet tissue, pericardial tissue, or crosslinked pericardial tissue. In certain embodiments, the pericardial tissue may be procured from bovine, equine, porcine, ovine, human, or other animals. In certain embodiments, the crosslinked pericardial tissue is crosslinked with a crosslinking agent selected from the group consisting of formaldehyde, glutaraldehyde, dialdehyde starch, glyceraldehydes, cyanamide, diimides, diisocyanates, dimethyl adipimidate, carbodiimide, epoxy compound, and mixture thereof.

The body 12, including annulus 18 and periphery 20, and support elements 16 are made of any suitable material such as super-elastic or elastic materials including thermal shape memory material. For instance, in certain embodiments of the present disclosure, suitable materials can include nickel titanium alloys such as Nitinol, other biocompatible shape memory metals, or shape memory polymers. The thermal shape memory material Nitinol, its shape transformation characteristics, and medical device uses are documented in prior art and well known to one of ordinary skilled in the art, and are described in U.S. Pat. No. 6,077,298 to Tu et al. and U.S. Pat. No. 6,890,350 to Walak, which are both incorporated by reference herein. Again, the body 12, annulus 18, and periphery 20 are configured so as enable movement at approximately the same time between first portions of the annulus and second portions of the annulus so that when each of the first portions are in a concave position, each of the second portions are in a convex position, and vice versa.

Each of the elements described herein can have its own size, height, shape, or construction material according to the need of the prosthetic valve or implantation sites. The prosthetic valve should be formed so as to have the required rigidity, stability, biocompatibility, and substantially seamless characteristics (such as leak-proof property) to support a functional valve.

When the prosthetic valve 12 is in its closed configuration, as depicted in FIG. 1, aspects of each second periphery portion 24 that are attached to each support element 16 are concave, and the support elements 16 are curved appropriately outward to keep the distal ends of the leaflets 14 tight to each other to define a seal 26, obstructing the flow from distal to proximal end of the valve 12 and maintaining the unidirectional function of the valve. Meanwhile, the first periphery portions 22 are each generally convex establishing an overall generally saddle-shape for the periphery 20.

When the valve 12 is in its open configuration, as depicted in FIG. 2, the aspects of each second periphery portion 24 that are attached to each support element 16 are deflected to a convex shape, and the support elements 16 are curved inward maximizing the distance between the distal ends of the leaflets 14 to maintain the utmost size of the opening 28 defined by the leaflets 14 to allow unidirectional flow. At generally the same time that the second periphery portions 24 move into a convex shape, the first periphery portions 22 each move into a generally concave shape establishing an overall generally saddle-shape geometry for the periphery 20.

In this regard, the valve of the present disclosure is designed so the saddle-shaped annulus can transform its shape due to pressure change. When the first periphery portions of the annulus moves from being generally concave to being generally convex, the second periphery portions of the annulus move from being generally convex to being generally concave, and vice versa.

The procedure for delivering the valve 10 includes a percutaneous manner, an endoscopic manner, a laparoscopic manner, a trans-apical manner, and the like. For instance, the valve 10 can be implanted surgically or delivered with minimally-invasive means such as through a major vessel such as femoral artery, carotid artery, jugular vein, subclavian vein, femoral vein, or any other suitable blood vessel. In certain heart valve replacement applications, the valve can be delivered and deployed in an open-chest operation, optionally combined with other surgical procedures. The valve 10 has a functional valvular configuration when it is deployed inside the heart, a blood vessel, a lymphatic vessel, or other body channel.

The valve can be loaded with at least one bioactive agent including analgesics/antipyretics, antiasthamatics, antibiotics, antidepressants, antidiabetics, antifungal agents, antihypertensive agents, anti-inflammatories, antineoplastics, anti-anxiety agents, immunosuppressive agents, antimigraine agents, sedatives/hypnotics, antipsychotic agents, antimanic agents, antiarrhythmics, antiarthritic agents, antigout agents, anticoagulants, thrombolytic agents, antifibrinolytic agents, antiplatelet agents and antibacterial agents, antiviral agents, antimicrobials, anti-infectives, and combination thereof. In certain embodiments, the valve can be loaded with at least one bioactive agent such as actinomycin D, paclitaxel, vincristin, methotrexate, angiopeptin, batimastat, halofuginone, sirolimus, tacrolimus, everolimus, tranilast, dexamethasone, mycophenolic acid, stem cells, and combinations thereof.

In certain embodiments, it is advantageous to implant the valve in an unexpanded orientation. In this regard, certain aspects of the valve can be modified as would be understood to one of ordinary skill in the art so as to allow the valve to more easily be implanted. If the valve is implanted in an unexpanded orientation, as would be understood in the art, the valve can be expanded by an inflatable balloon that is in fluid communication to inflatable fluid outside of the body through a lumen of the delivery apparatus. In certain embodiments, the valve 10 can be expanded using a shape memory material (metallic or non-metallic), such as those materials described previously. The shape recovery (or shape transition) temperature of a shape memory material (e.g., Nitinol) is distinct from the living body temperature, for example, a shape recovery temperature at about 38 to 55° C., preferably between about 40 and 45° C. In certain embodiments, the temperature elevation could be provided by connecting the valve to an external radiofrequency source through an insulated wire, wherein the distal end of the wire is un-insulated and functions as an electrode that lies beneath and removably connected to the unexpanded valve. Under a pre-determined power level and power duration, the electrode delivers adequate radiofrequency energy to raise the valve temperature to above the shape recovery temperature of the construction material. In an alternate embodiment, a dose of hot saline may be injected to raise the valve temperature to above the shape recovery temperature of the construction material.

Figure 1A:
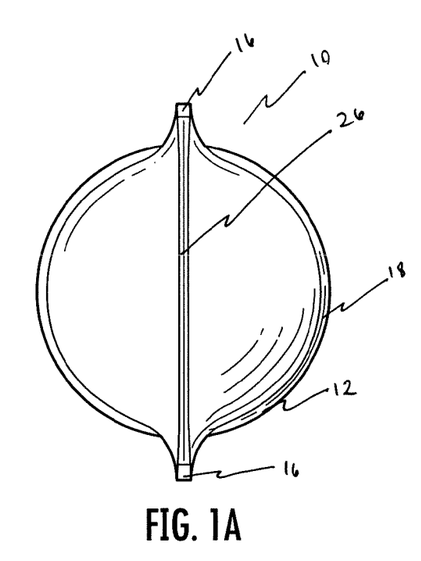
Figure 1B:
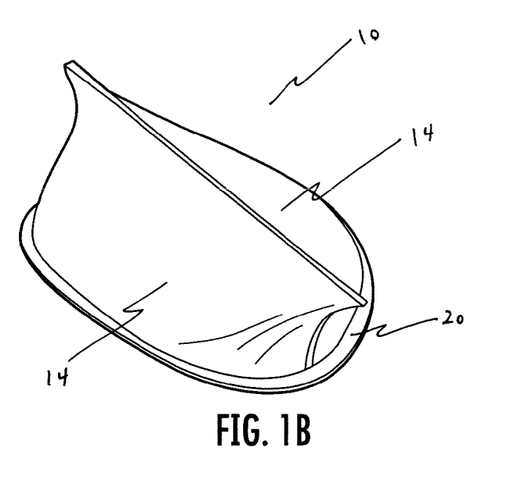
Figure 1C:
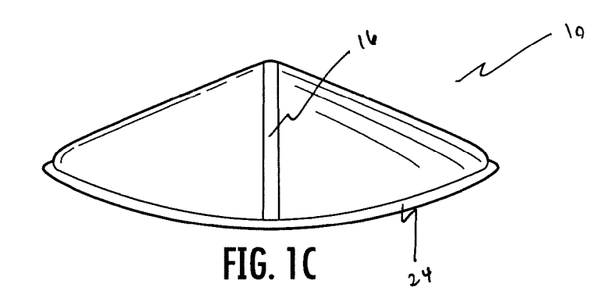
Figure 1D:
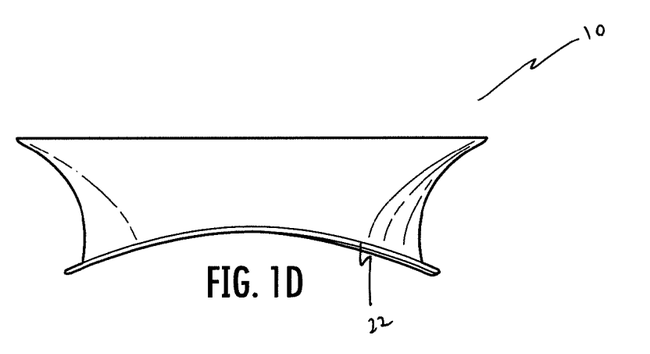
Figure 2A:
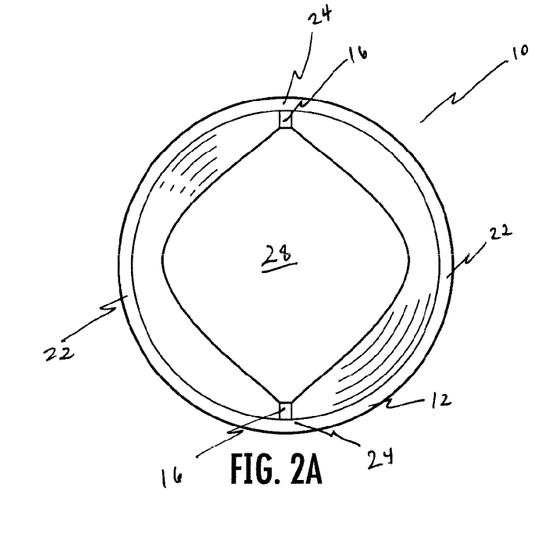
Figure 2B:
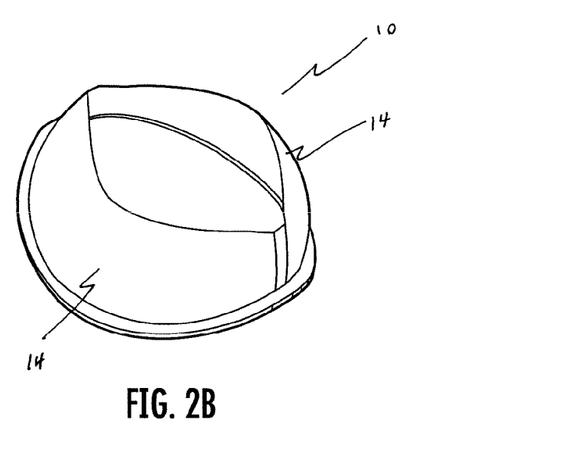
Figure 2C:
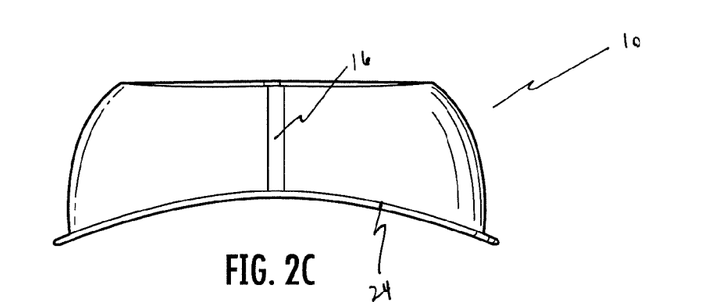
Figure 2D:
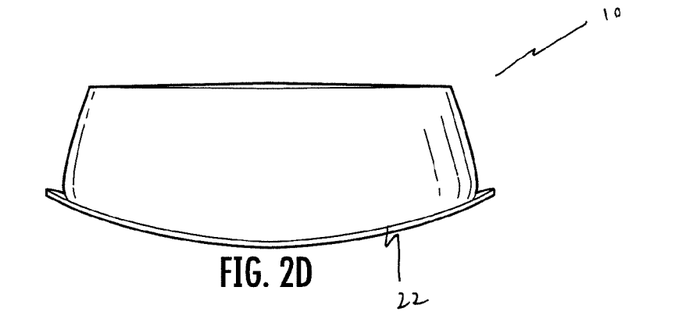
Figure 3:
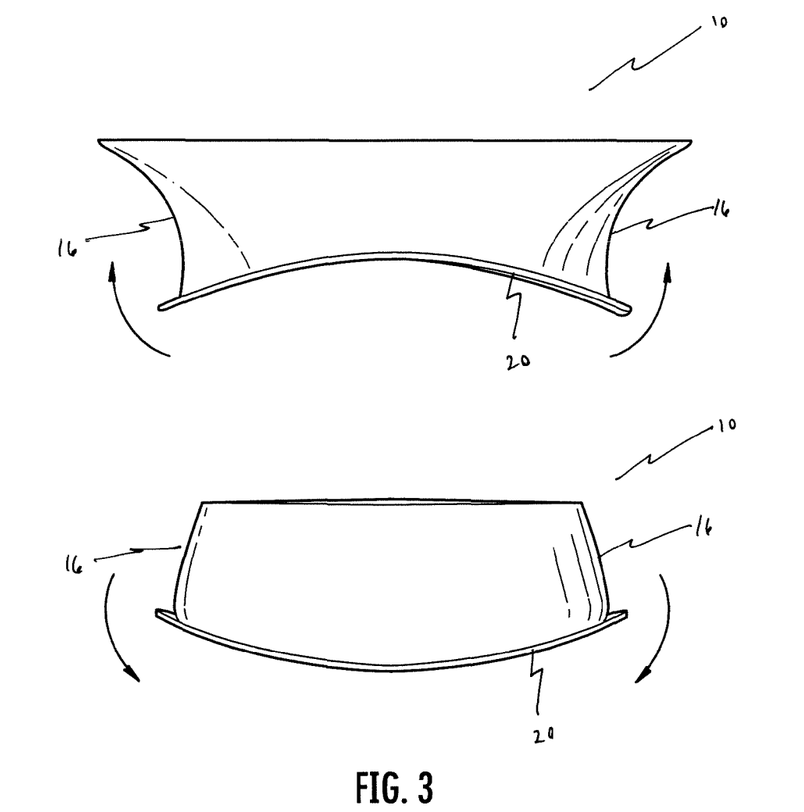
FIG. 3 illustrates a geometrical transition of a prosthetic valve due to changes in the shape of the saddle-shaped base in accordance with certain embodiments of the present disclosure.

Turning now to certain heart valve applications, when the valve of the present disclosure is implanted in a mitral position, portions of the periphery 20 are deflected due to pressure change and such a geometrical transformation results in opening or closure of the valve during diastole or systole, respectively, as depicted in FIG. 3. The periphery is configured so as enable movement at approximately the same time between first portions and second portions so that when each of the first portions are in a concave position, each of the second portions are in a convex position, and vice versa. The change in the angle of support elements 16 with respect to the axis of the saddle-shaped annulus periphery 20 maintains the valve 10 in an open or closed position. The support elements 16 can also prevent leaflets 14 from being prolapsed into the left atrium during systole.

When the valve 10 is implanted in an aortic position and deployed, portions of the periphery 20 are deflected due to pressure change and such a geometrical change results in opening or closure of the valve during systole or diastole, respectively. Again, the change in the angle of support elements 16 with respect to the axis of the saddle-shaped annulus periphery 20 also assists in maintaining the valve open or closed. The support elements 16 can also prevent leaflets 14 from being prolapsed into the left ventricle (LV) during diastole when the LV pressure is dropping. Such valves in accordance with the present disclosure can, among numerous other applications, also be implanted as replacement for right sided heart valves such as the pulmonary and the tricuspid valves.

In the interests of brevity and conciseness, any ranges of values set forth in this specification are to be construed as written description support for claims reciting any sub-ranges having endpoints which are whole number values within the specified range in question. By way of a hypothetical illustrative example, a disclosure in this specification of a range of 1-5 shall be considered to support claims to any of the following sub-ranges: 1-4; 1-3; 1-2; 2-5; 2-4; 2-3; 3-5; 3-4; and 4-5.

These and other modifications and variations to the present disclosure can be practiced by those of ordinary skill in the art, without departing from the spirit and scope of the present disclosure, which is more particularly set forth in the appended claims. In addition, it should be understood that aspects of the various embodiments can be interchanged both in whole or in part. Furthermore, those of ordinary skill in the art will appreciate that the foregoing description is by way of example only, and is not intended to limit the disclosure.

What is claimed is:

1. A prosthetic valve consisting of:
a saddle-shaped annulus, a pair of leaflets connected to the annulus, and a pair of support elements, each of the support elements connected to the leaflets, each of the leaflets separated from one another by each support element, the annulus adapted to move back and forth from a generally concave state to a generally convex state, the pair of leaflets adapted to define an opening when the annulus is in the generally concave state and to define a seal when the annulus is in the generally convex state;
wherein when the valve is implanted in a mitral position, pressure change between diastole and systole cause a geometrical change resulting in opening and closure of the valve leaflets, respectively, with annulus deflection.

2. The prosthetic valve of claim 1, wherein the annulus and the pair of support elements comprise a shape memory material.

3. The prosthetic valve of claim 2, wherein the shape memory material comprises a nickel titanium alloy.

4. The prosthetic valve of claim 1, wherein the pair of leaflets comprise synthetic material, engineered biological tissue, biological valvular leaflet tissue, pericardial tissue, cross-linked pericardial tissue, or combinations thereof.

5. The prosthetic valve of claim 4, wherein the pair of leaflets comprise pericardial tissue selected from the group consisting of bovine, equine, porcine, ovine, human tissue, or combinations thereof.

6. The prosthetic valve of claim 4, wherein the material or tissue comprises a compliant membrane of a single sheet or a compound manifold.

7. The prosthetic valve of claim 1, wherein the support elements are curved away from one another when the pair of leaflets define the seal.

8. The prosthetic valve of claim 1, wherein the support elements are curved towards one another when the pair of leaflets define the opening.

* * * * *